(12) United States Patent
Masters et al.

(10) Patent No.: US 8,536,037 B2
(45) Date of Patent: Sep. 17, 2013

(54) ELECTRICALLY RESPONSIVE DEVICE

(75) Inventors: Brett P. Masters, Watertown, MA (US); Michael F. Miller, Hollis, NH (US)

(73) Assignee: Bioscale, Inc., Cambridge, MA (US)

( * ) Notice: Subject to any disclaimer, the term of this patent is extended or adjusted under 35 U.S.C. 154(b) by 1339 days.

(21) Appl. No.: 11/398,308

(22) Filed: Apr. 5, 2006

(65) Prior Publication Data

US 2006/0228657 A1   Oct. 12, 2006

Related U.S. Application Data

(60) Provisional application No. 60/668,933, filed on Apr. 6, 2005.

(51) Int. Cl.
*G01T 1/00* (2006.01)

(52) U.S. Cl.
USPC ............................................. 438/584

(58) Field of Classification Search
USPC ..................................... 438/584; 430/954
See application file for complete search history.

(56) References Cited

U.S. PATENT DOCUMENTS

| | | | | |
|---|---|---|---|---|
| 4,278,492 A | | 7/1981 | Cross et al. | 156/627 |
| 4,364,016 A | * | 12/1982 | Tanski | 333/193 |
| 4,952,832 A | * | 8/1990 | Imai et al. | 310/313 A |
| 5,129,262 A | | 7/1992 | White et al. | 73/599 |
| 5,189,914 A | | 3/1993 | White et al. | 73/599 |
| 5,490,034 A | | 2/1996 | Zavracky et al. | 361/283.4 |
| 5,668,303 A | | 9/1997 | Giesler et al. | 73/24.06 |
| 5,836,203 A | | 11/1998 | Martin et al. | 73/579 |
| 6,091,182 A | | 7/2000 | Takeuchi et al. | 310/330 |
| 6,323,580 B1 | | 11/2001 | Bernstein | 310/324 |
| 6,455,980 B1 | | 9/2002 | Bernstein | 310/324 |
| 6,506,620 B1 | | 1/2003 | Scharf et al. | 438/52 |
| 6,511,915 B2 | | 1/2003 | Mlcak | 438/695 |
| 6,673,694 B2 | | 1/2004 | Borenstein | 438/411 |
| 6,688,158 B2 | | 2/2004 | Cunningham et al. | 73/24.06 |
| 6,837,097 B2 | | 1/2005 | Cunningham et al. | 73/24.06 |
| 6,851,297 B2 | | 2/2005 | Cunningham et al. | 73/24.06 |
| 6,946,314 B2 | | 9/2005 | Sawyer et al. | 438/50 |
| 7,000,453 B2 | | 2/2006 | Cunningham et al. | 73/24.06 |
| 2003/0020367 A1 | * | 1/2003 | Maeda et al. | 310/313 D |
| 2005/0082944 A1 | | 4/2005 | Thompson et al. | 310/318 |
| 2005/0148147 A1 | | 7/2005 | Keating et al. | 438/299 |

OTHER PUBLICATIONS

Roederer, J.E.; Bastiaans, G.J."Micrograimetric Immunoassay with Piezoelectric Crystals." Anal. Chem. 1983, 55, pp. 2333-2396.*
Sportsman, J.R.; Wilson, G. S. "Chromatographic properties of silica-immobilized antibodies." Anal. Chem. 1980, 52, pp. 2013-2018.*
"Project Lead the way; Forging new generations of Engineers." 21 pages. Date unkown.*

(Continued)

*Primary Examiner* — Christine T Mui
(74) *Attorney, Agent, or Firm* — Proskauer Rose LLP

(57) ABSTRACT

Electrically responsive devices and methods for fabricating electrically responsive devices involves applying an electrically responsive material (e.g., an electroactive material) over at least a portion of a surface of a substrate material and applying an electrode material over at least a portion of a surface of the electrically responsive material. At least one region of the electrode material is selectively removed exposing the electrically responsive material. At least some of the electrically responsive material is selectively removed in a region corresponding to the at least one region of the electrode material.

18 Claims, 6 Drawing Sheets

(56) References Cited

OTHER PUBLICATIONS

"Physical Science in Education, Properties of Matter," 2000, Schlessinger Media, 2 pages.*
Dubé et al., "A Si-Based FPW Sensor Array System with Polymer Microfluidics Integrated on a PCB", 2002 IEEE, pp. 460-465.
*The RF and Microwave Handbook*, Chapter 6, "Passive Technologies," Sections 6.1-6.5, CRC Press LLC, 2001, pp. 6-2-6-83.
R. M. White, "Direct Piezoelectric Coupling to Surface Elastic Waves," Applied Physics Letters, vol. 7 (Dec. 15, 1965), pp. 314-316.
J. F. Dias et al., "Frequency/Stress Sensitivity of S.A.W. Resonators," Electronics Letters, vol. 12, No. 22, Oct. 1976, pp. 580-582.
S. W. Wenzel, "Applications of Ultrasonic Lamb Waves," dissertation submitted in partial satisfaction of the requirements for the degree of Doctor of Philosophy in Engineering/Electrical Engineering and Computer Sciences, University of California at Davis (1992).
J. Neumeister et al., "A SAW Delay-line Oscillator as a High-resolution Temperature Sensor," Sensors and Actuators, (Mar. 1990), pp. 670-672.
W. C. Tang, "Electrostatic Comb Drive for Resonant Sensor and Actuator Applications," Ph.D. Thesis, Electrical Engineering and Computer Sciences, University of California Berkeley, Berkeley, CA, Nov. 1990.
R. L. Baer et al., "Phase Noise Measurements of Flexural Plate Wave Ultrasonic Sensors," 1991 IEEE Ultrasonics Symposium, 1991, pp. 321-326.
J. W. Grate et al., "Flexural Plate Wave Devices for Chemical Analysis," Analytical Chemistry, vol. 63, 1991, pp. 1552-1561.
Gianchandani et al., "A Bulk Silicon Dissolved Wafer Process for Microelectromechanical Devices," Journal of Microelectromechanical Systems, vol. 1, No. 2, Jun. 1992, pp. 77-85.
J. W. Grate et al., "Frequency-Independent and Frequency-Dependent Polymer Transitions Observed on Flexural Plate Wave Ultrasonic Sensors," Analytical Chemistry, vol. 64, 1992, pp. 413-423.
Giesler et al., "Electrostatic excitation and capacitive detection of flexural plate-waves," Sensors and Actuators A, vol. 36, 1993, pp. 113-119.
J. W. Grate et al., "Acoustic Wave Microsensors—Part I" Analytical Chemistry, vol. 65, No. 21, Nov. 1, 1993, pp. 940A-948A.
J. W. Grate et al., "Acoustic Wave Microsensors—Part II" Analytical Chemistry, vol. 65, No. 22, Nov. 15, 1993, pp. 987A-996A.
J. W. Grate et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition," Analytical Chemistry, vol. 65, No. 14, Jul. 15, 1993, pp. 1868-1881.
E.H. Yang et al., Sensors and Actuators, vol. 50 (1995), pp. 151-156.
K. R. Williams, et al., "Etch Rates for Micromachining Processing," Journal of Microelectromechnical Systems, vol. 5, No. 4, Dec. 1996, pp. 256-269.
A. F. Collings et al., "Biosensors: recent advances," Rep. Prog. Phys., vol. 60, 1997, pp. 1397-1445.
R. M. White, "Introductory Lecture—Acoustic interactions from Faraday's crispations to MEMS," Faraday Discuss, vol. 107 (1997), pp. 1-13.
D. S. Ballantine, Jr. et al., "Acoustic Wave Sensors—*Theory, Design, and Physico-Chemical Applications*," Academic Press, New York, 1997.
J. C. Pyun et al., "Development of a biosensor for *E. coli* based on a flexural plate wave (FPW) transducer," Biosensors & Bioelectronics, vol. 13, 1998, pp. 839-845.
N. Yazdi et al., "Micromachined Inertial Sensors," Proceedings of the IEEE, vol. 86, No. 8, Aug. 1998, pp. 1640-1659.
A. W. Wang et al., "A Silicon-based Immunoassay for Detection of Breast Cancer Antigens," Sensors and Actuators B, vol. 49 (1998), pp. 13-21.
S. E. Cowan et al., "Ultrasonic Flexural-Plate-Wave Sensor for Detecting the Concentration of Settling *E. coli* W3110 Cells," Analytical Chemistry, vol. 71, No. 16, Aug. 15, 1999, pp. 3622-3625.
A. Janshoff et al., "Piezoelectric Mass-Sensing Devices as Biosensors—An Alternative to Optical Biosensors?," Angew. Chem. Int. Ed., vol. 39, 2000, pp. 4004-4032.
J. Choi et al., "A new magnetic bead-based, filterless bio-separator with planar electromagnet surfaces for integrated bio-detection systems," Sensors and Actuators B, vol. 68, 2000, pp. 34-39.
M. S. Weinberg et al., "Modeling Flexural Plate Wave Devices," Journal of Microelectromechanical Systems, vol. 9 (Sep. 2000), pp. 370-379.
B. Cunningham et al., "Design, fabrication and vapor characterization of a microfabricated flexural plate resonator sensor and application to integrated sensor arrays," Sensors and Actuators B, vol. 73, 2001, pp. 112-123.
K. M. Lakin, "Thin Film Resonators and High Frequency Filters," TFR Technologies, Inc., (Jun. 1, 2001), pp. 1-18.
F. Engelmark, "AlN and High-k Thin Films for IC and Electroacoustic Applications," Comprehensive Summaries of Uppsala Dissertations from the Faculty of Science and Technology, vol. 757, ACTA Universitatis Upsaliensis, Uppsala, 2002.
K. Williams, et al., "Etch Rates for Micromachining Processing—Part II," Journal of Microelectromechnical Systems, vol. 12, No. 6, Dec. 2003, pp. 761-778.
D. Carter et al., "Fabrication and Measurement of an IC-Compatible GHZ-Range Piezoelectric Longitudinal Bar Resonator," Solid-State Sensor, Actuator and Microsystems Workshop, Hilton Head Island, South Carolina, Jun. 6-10, 2004, pp. 254-257.
J. H. Lee et al., "Effect of mass and stress on resonant frequency shift of functionalized $Pb(Zr_{0.52}Ti_{0.48})O_3$ thin film microcantilver for the detection of C-reactive protein," Applied Physics Letters, vol. 84, No. 16, Apr. 19, 2004, pp. 3187-3189.
G. Chapman et al, "Bi/In Thermal Resist for Both Si Anisotropic Wet Etching and $Si/SiO_2$ Plasma Etching," SPIE Micro04, Photonics West, Micromachining and Microfabrication Process Technology IX, vol. 5342, 2004.
V. Milanovic, "Multilevel Beam SOI-MEMS Fabrication and Applications," Journal of Microelectromechanical Systems, vol. 13, (Feb. 2004) pp. 19-30.
K. S. Ryu et al., "Precision Patterning of PDMS Thin Films: A New Fabrication Method and Its Applications," International Symposium on Micro Total Analysis System (uTAS), Nara, Japan, 2002.
Madou, M., "Fundamentals of Microfabrication," CRC Press, 1997.
B. J. Costello et al., "A Flexural-Plate-Wave Microbial Sensor," 1992 IEEE, pp. 69-72.
S. W. Wenzel, "A Multisensor Employing an Ultrasonic Lamb-Wave Oscillator," IEEE Transactions on Electron Devices, vol. 35, No. 6, Jun. 1988, pp. 735-743.
M. A. Dubois, "Thin Film Bulk Acoustic Wave Resonators: A Technology Overview," MEMSWAVE 03, Toulouse, France, Jul. 2-4, 2003.

* cited by examiner

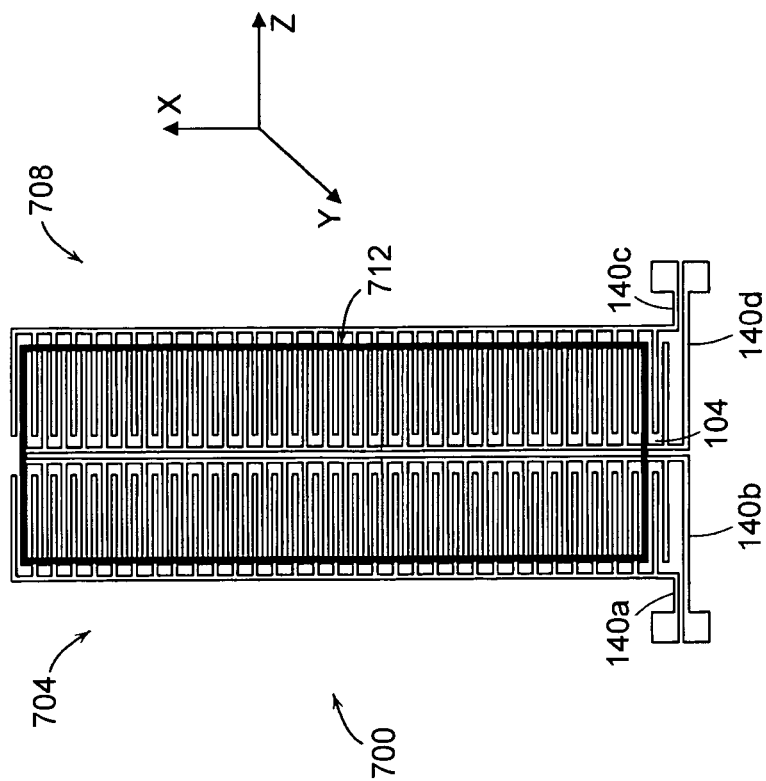
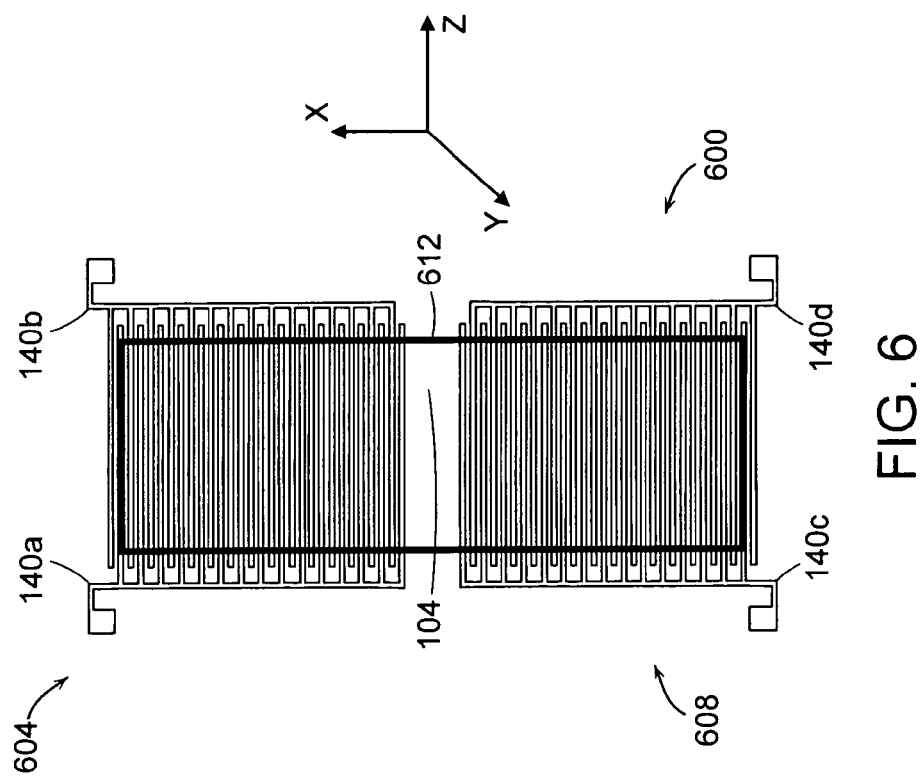
FIG. 7
FIG. 6

ELECTRICALLY RESPONSIVE DEVICE

RELATED APPLICATIONS

This application claims priority to U.S. provisional application Ser. No. 60/668,933, filed on Apr. 6, 2005, and entitled "Micromachined Electroactive Resonant Device," the entirety of which is hereby incorporated herein by reference.

FIELD OF THE INVENTION

The present invention generally relates to electrically responsive devices and methods for fabricating electrically responsive devices.

BACKGROUND OF THE INVENTION

Electrically responsive devices are those devices that generate an output signal in response to an electrical signal and/or generate an electrical signal in response to an input signal. Typical types of input and output signals include electrical, optical, electromagnetic, vibrational, and thermal signals. One type of electrically responsive devices is a resonant device.

Resonant devices, such as surface acoustic wave devices, bulk acoustic wave devices, flexural plate/lamb wave devices, and quartz crystal microbalance devices are fashioned substantially from monolithic materials such as quartz, or, from layered materials that include uniform thin films of electroactive materials (e.g., piezoelectric materials such as Zinc Oxide, Lead Zirconate Titanate—PZT, Aluminum Nitride, Indium Nitride and Sol-Gel piezoceramic materials) in combination with other micromachinable materials (e.g., Silicon, Silicon Oxides, Silicon Nitride and Nickel Irons). These resonant devices, when preferentially coated with appropriate materials and/or packaged in an appropriate environment are used as, for example, electrical filters (e.g., passive), gas phase detectors, and liquid phase sensors.

As an electrical filter the resonant device is used to transmit resonant energy and filter signals outside of the pass band of the device. Electrical filters (e.g., surface acoustic wave (SAW) devices and film bulk acoustic resonator (FBAR) devices) are typically characterized by their insertion, transmission and reflectance properties. High transmission, isolated narrow band and stable properties of resonance operation are desirable features for filters used in modulating and demodulating wired and wireless signals. Defined and stable narrow pass band filter properties allow for packing more carrier frequencies in a given bandwidth.

Resonant devices also are sometimes used to determine the presence and amount of various measurands (e.g., chemical or biological) in gas phase and liquid phase samples. Resonant sensors may be used, for example, to determine the presence and magnitude of chemical vapors and biological matter in aerosol, the bulk properties of liquids (e.g., density, viscosity, and speed of sound) and the concentration of analytes in solutions.

In gas phase operation, a surface of a resonant device is typically coated with an absorbent material that interacts selectively and binds with specific gas phase products passed over the surface of the resonant device. The gas phase products that bind to the absorbent material increase the mass loading of the resonant device. The increase in mass loading changes properties of the device (e.g., the stiffness or the resonance of the device). Electrical signals produced by the resonant device reflect the change in resonance of the device.

In liquid operation, a surface of a resonant device is exposed to a liquid. The surface of the resonant device interacts with and is subsequently loaded by the physical interaction of the liquid with the resonant device. In some devices the loading of the resonant device occurs through the coherent oscillatory compression and motion of the liquid near the surface of the device. The resonant device produces an electrical signal that varies as the loading varies. A detectable resonance response results if the motion of the liquid is stable and oscillatory, and the oscillatory motion dissipates substantially less than the peak stored potential energy of the moving surface of the resonant device. Changes in the properties of the liquid are determined based on the electrical signal produced by the resonant device.

Generally, it is desirable for resonant devices to have isolated resonance modes, narrow pass bands, low loss, and stable and repeatable operating characteristics when used in a variety of operating environments (e.g., vacuum, gas phase, and liquid phase). Variations in the devices (e.g., due to manufacturing tolerances) tend to result in non-isolated resonance modes, wide resonance bands, high loss, and unstable and non-repeatable operating characteristics.

A need therefore exists for improved electrically responsive devices and methods for fabricating electrically responsive devices.

SUMMARY OF THE INVENTION

The present invention features electrically responsive devices and methods for fabricating electrically responsive devices. In some embodiments, the present invention features resonant devices and methods for fabricating resonant devices.

The invention, in one aspect, features a device with spatially modulated structural properties. Excitation and/or sensing means of the device are substantially correlated with the modulated structural properties. Selective modulation of structural properties (e.g., stiffness and mass properties) results in preferred resonance mode shapes. For example, correlating the excitation means with the structural modulation selectively excites preferred resonances resulting in a preferred pass band. Correlating the sensing means with the structural modulation enables selective sensing of preferred resonances, also resulting in a preferred pass band.

In one embodiment, correlating excitation and sensing means with the structural property modulation of a device results in an electrical filter (e.g., a surface acoustic wave (SAW) device or a film bulk acoustic resonator (FBAR) device) having a preferred pass band, narrower bandwidth and lower transmission loss than would otherwise be achieved without structural modifications. The pass band includes at least one resonant mode.

In some embodiments, preferred stiffness and mass modulations are achieved by selectively removing and/or adding material to a substantially planar device. The modulation can be periodic with spatial periodicity set to match (or substantially match) one of the device's mode shapes.

In some embodiments, the device is a composite of materials that is fabricated having modulated structural properties. In some embodiments, the device has a substantially uniform thickness. By way of example, a device can be fabricated having uniform thickness by removing a first material of the device and then filling the region exposed by removing the first material with a second material that has a different stiffness than the first material.

In one embodiment, the device includes electrode material, electroactive material, and a substrate material, according to an illustrative embodiment of the invention. The electroactive material is combined with the substrate material to achieve composite structural properties in which the properties (e.g., stiffness and/or mass) vary along the device to achieve preferred device properties. A preferred excitation and sensing mode is achieved by applying (e.g., depositing) electrode material to the electroactive material over a substantial area of the device. In some embodiments, alternative materials are instead used to fabricate devices incorporating principles of the present invention. For example, materials that allow for electrostatic or capacitive excitation and/or sensing can be used to fabricate a device.

The invention, in another aspect, relates to a method for fabricating an electrically responsive (e.g., resonant) device. The method involves applying an electrically responsive (e.g., electroactive or electrooptical) material over at least a portion of a surface of a substrate material and applying an electrode material over at least a portion of a surface of the electrically responsive material. The method also involves selectively removing at least one region of the electrode material exposing the electrically responsive material. The method also involves selectively removing at least some of the electrically responsive material in a region corresponding to the at least one region of the electrode material (i.e., the region exposed by removing the electrode material).

In some embodiments, the selective removal of the electrode material and the removal of the electrically responsive material substantially improves the band pass resonant response (e.g., modes greater than the first mode) of the device.

In some embodiments, the invention relates to a method for modifying a resonance mode of the response of the device by enforcing that resonance mode of response of the device. In some embodiments, a particular pattern of the electrode material is used to enforce a resonance mode of response of the device. In some embodiments, removal of the electrically responsive material substantially modifies at least one resonance mode of response of the device by reducing modal overlap and spillover associated with other resonance modes of the device.

In some embodiments, the method also can involve selectively removing at least some of the substrate material in a region corresponding to the at least one region of the electrode material. The removal of the electrode material and the removal of the electrically responsive material can involve etch processing (one or more of wet etching, dry etching, plasma etching, laser assisted etching, laser ablation, ion beam milling, and electron beam etching).

Removal of the electrode material and removal of the electrically responsive material can be conducted with a single removal step (e.g., a single etching step is performed that removes the material). Removal of the electrode material can involve producing an interdigitated pattern in the electrode. Applying the electrically responsive material over the surface of the substrate material can involve applying the electrically responsive material on to the surface of the substrate material by, for example, reactive sputtering of the electrically responsive material.

Applying the electrode material over the surface of the electrically responsive material can involve applying the electrode material on to the surface of the electrically responsive material. In some embodiments, the electrode material is applied by physical vapor deposition (e.g., e-beam evaporation plating or sputtering). In some embodiments, an electrode material is also applied between the substrate material and the electrically responsive material.

In some embodiments, selectively removing the electrically responsive material in the region corresponding to the at least one region of the electrode material includes removing all the electrically responsive material in the region corresponding to the at least one region of the electrode material. In some embodiments, an alternative material is then applied to the regions from which the electrode material and the electrically responsive material were removed to produce a device having a substantially uniform thickness while still having modulated stiffness and/or mass properties, in accordance with principles of the present invention.

In some embodiments, the method also can involve selectively removing a portion of the substrate material. Selectively removing a portion of the substrate material can result in the electrically responsive material having at least one region that is unsupported by the substrate. In some embodiments, the unsupported electrically responsive material is a cantilever electrically responsive element. The electrically responsive material can include, for example, an electroactive material (e.g., a piezoelectric material, piezoceramic material, electroceramic material or a single crystal electroactive material).

The combination of the substrate, electrically responsive material and electrode material can be incorporated into an integrated circuit package. The device fabricated according to the method can be a filter or a sensor (e.g., physical, biological or chemical sensor).

In some embodiments, a filler material is applied in the region of the electrically responsive material that was previously selectively removed. The filler material can have a stiffness dissimilar to the stiffness of the electrically responsive material.

The invention, in another aspect, relates to a method for fabricating an electrically responsive device (e.g., a resonant device) that involves applying an electrode material over at least a portion of a surface of an electrically responsive material. The method also involves selectively removing at least one region of the electrode material exposing the electrically responsive material. The method also involves selectively removing at least some of the electrically responsive material in a region corresponding to the at least one region of the electrode material to substantially modify at least one resonance mode of the device.

The invention, in another aspect, relates to a method for fabricating an electrically responsive device. The method involves selectively applying electrically responsive material to a surface of a substrate material and selectively applying an electrode material to a surface of the electrically responsive material to substantially modify at least one resonance mode of response of the device.

The invention, in another aspect, features an electrically responsive device. The device includes a substrate material and at least one electrically responsive element on the substrate. The device also includes an electrode material on a surface of the at least one electrically responsive element, wherein the electrically responsive element and the electrode material are configured to modify at least one resonance mode of response of the device.

The invention, in another aspect, features an electrically responsive device that includes a substrate material and at least one electrically responsive element on the substrate. The device also includes an electrode material on a surface of the at least one electrically responsive element, wherein the electrically responsive element and the electrode material are patterned on the substrate layer to modify at least one resonance mode of response of the device by reducing modal overlap and spillover associated with other resonance modes of the device.

In some embodiments, the electrically responsive material and electrode material are patterned to produce at least one actuating element and at least one sensing element. In some embodiments, the electrically responsive material and electrode material are patterned to produce at least one launch element and at least one receiver element. The resonant device can include a conductive (e.g., metallic) material between the electrically responsive material and the substrate material.

The invention, in another aspect, features an electrically responsive device that includes a substrate material having a surface and defining a plane. The device also includes an electrically responsive material over at least a portion of the surface of the substrate material and varying in thickness in the plane of the substrate material. The device also includes an electrode material over portions of the surface of the electrically responsive material in an interdigitated pattern.

In some embodiments, the electrode material regions are located over thicker regions of the electrically responsive material. In some embodiments, the electrode material regions are located over thinner regions of the electrically responsive material.

The invention, in another aspect, features an electrically responsive device. The device includes a substrate material having a surface and varying in thickness in a plane of the substrate material. The device also includes an electrically responsive material over at least a portion of the surface of the substrate material. The device also includes an electrode material over portions of the surface of the electrically responsive material in an interdigitated pattern.

The invention, in another aspect, relates to a method for fabricating an electrically responsive device. The method involves applying an electrically responsive material over at least a portion of a surface of a substrate material. The method also involves selectively removing at least some of the electrically responsive material. The method also involves applying an electrode material over at least a portion of a surface of the electrically responsive material.

In some embodiments, applying the electrode material produces an interdigitated electrode pattern over the electrically responsive material. In some embodiments, applying the electrode material produces an annular-shaped electrode pattern over the electrically responsive material.

The invention, in another aspect, relates to a method for fabricating an electrically responsive device. The method involves applying a first electrode material over at least a portion of a surface of a substrate material and applying an electrically responsive material over at least a portion of a surface of the first electrode material. The method also involves applying a second electrode material over at least a portion of a surface of the electrically responsive material. The method also involves selectively removing some of at least one of the electrically responsive material or the substrate material to modify at least one resonance mode of response of the device.

The invention, in another aspect, features an apparatus for detection of an analyte. The apparatus includes a fluid channel. The apparatus also includes an electrically responsive device defining at least a portion of at least one surface of the fluid channel. The apparatus also includes a monitoring device to monitor at least one signal output by the device. The device includes a substrate material having a surface and defining a plane. The device also includes an electrically responsive material over at least a portion of the surface of the substrate material and varying in thickness in the plane of the substrate material. The device also includes an electrode material over portions of the surface of the electrically responsive material in an interdigitated pattern.

The invention, in another aspect, features a cartridge for detection of an analyte. The cartridge includes a fluid channel and an electrically responsive device (e.g., a resonant device) located within the fluid channel or defining at least a portion of at least one surface of the fluid channel. The device includes a substrate material having a surface and defining a plane. The device also includes an electrically responsive material over a portion of the surface of the substrate material and varying in thickness in the plane of the substrate material. The device also includes an electrode material over portions of the surface of the electrically responsive material in an interdigitated pattern.

The invention, in another aspect, features a kit used in detection of an analyte. The kit includes a cartridge that has a fluid channel and a first component which specifically binds the analyte to a surface of the device. The cartridge also includes an electrically responsive device (e.g., a resonant device) located within the fluid channel or defining at least a portion of at least one surface of the fluid channel. The device includes a substrate material having a surface and defining a plane. The device also includes an electrically responsive material over a portion of the surface of the substrate material and varying in thickness in the plane of the substrate material. The device also includes an electrode material over portions of the surface of the electrically responsive material in an interdigitated pattern. The kit also includes particles (e.g., magnetic beads) that have a second component that specifically bind the analyte.

The invention, in another aspect, relates to a method for fabricating an electrically responsive device. The method involves providing an electrically responsive material over at least a portion of a substrate material. The method also involves altering a property (e.g., a structural property) of at least one of the electrically responsive material or the substrate material to isolate a resonant mode of the device.

Altering a property can involve altering the stiffness over a portion of the electrically responsive material or the substrate material. Altering a property can involve altering distribution of mass over a portion of the electrically responsive material or the substrate material. Altering a property can involve removing a portion of the electrically responsive material to correspond substantially with an electrode pattern on a surface of the electrically responsive material.

The invention, in another aspect, features an electrically responsive device. The device includes a substrate material. The device also includes an electrically responsive material over at least a portion of the substrate, wherein a property of at least one of the substrate material or the electrically responsive material is altered to isolate a resonant mode of the device by altering the stiffness of the device.

The invention, in another aspect, relates to a method for fabricating an electrically responsive device. The method involves applying an electrically responsive material over at least a portion of a surface of a substrate material. The method also involves applying an electrode material over at least a portion of a surface of the electrically responsive material. The method also involves applying a material over at least a portion of the surface of the device to alter mass distribution over the device to substantially modify at least one resonance mode of response of the device.

The invention, in another aspect, features an electrically responsive device including a composite structure having spatially modulated properties. The device also includes means of exciting and sensing motion of the structure that is substantially correlated with the spatially modulated properties to produce a narrow (e.g., with respect to frequency) and low loss (e.g., having a more pronounced transfer function peak) pass band. Advantages according to the invention can be achieved in devices exposed to fluid loading or in devices not exposed to fluid loading.

In some embodiments, the composite structure includes an electroactive material. In some embodiments, the spatially modulated properties are periodic along a surface of the structure. In some embodiments, the composite structure includes a component capable of binding to biological or chemical matter.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

FIG. 6 is a schematic illustration of a pattern of electrode material, according to an illustrative embodiment of the invention.

FIG. 7 is a schematic illustration of a pattern of electrode material, according to an illustrative embodiment of the invention.

DETAILED DESCRIPTION OF ILLUSTRATIVE EMBODIMENTS

Figure 1A:
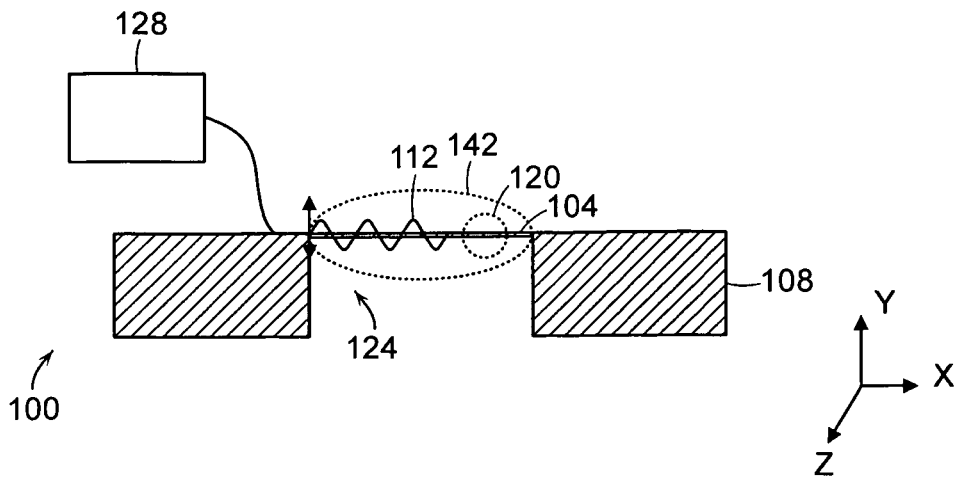
FIG. 1A is a schematic illustration of an electrically responsive device.

FIG. 1A is a schematic illustration of an electrically responsive device 100. In this embodiment, the electrically responsive device 100 is a resonant device constructed from a substrate 108 (e.g., a silicon wafer) using micro-fabrication techniques known in the art. Alternative methods of fabrication are possible without departing from the scope of the present invention. In this embodiment, a cavity 124 is etched into the substrate 108 to produce a thin, suspended membrane 104 that is approximately 1.6 mm long (along the X-Axis), 0.3 mm wide (along the Z-Axis) and 2 µm thick (along the Y-Axis). The overall substrate 108 thickness is approximately 500 µm, so the depth of the cavity 124 is just slightly less than the substrate 108 thickness. A 0.5 µm layer of an electrically responsive material 132 (e.g., an electroactive or electrooptical material) is deposited over an outer surface 160 (i.e., the surface opposite the cavity 124) of the membrane 104, as shown in a region 120 of the device 100 shown in the expanded view insert of FIG. 1B. In some embodiments, a fluid channel is used instead of a cavity 124, in which the fluid channel, for example, delivers fluid to the membrane 104 and/or directs fluid away from the membrane 104.

In some embodiments, the electrically responsive device is fabricated from a variety of materials forming a composite structure. The device also includes actuation and sensing structure that allows for actuation of the composite structure and sensing motion of the composite structure, respectively. In one embodiment, the composite structure is the suspended structure 142 shown in FIG. 1 including region 120 of FIG. 2).

The electrically responsive material 132 can be, for example, an electroactive material (e.g., a piezoelectric material, a piezoceramic material, an electroceramic material or a single crystal electroactive material). In one embodiment, the electroactive material is aluminum nitride (AlN). Electrode material in the form of two sets of interdigitated metal electrode material 140 are deposited over an outer surface 164 of the electrically responsive material 132. In some embodiments, titanium and/or gold are suitable electrode materials. In one embodiment, a 100 Angstrom layer of titanium is used as the electrode material 140. In some embodiments, a thin layer of metal (e.g., gold) is deposited over an outer surface 164 of the electroactive material 132 prior to deposition of the electrode material 140.

In this embodiment, the substrate 108 forming the membrane 104 is silicon. The silicon membrane 104 is conductive preferably with a resistivity of less than about 0.01 ohm-cm. The membrane 104 functions as a lower electrode. A field is applied between one set of the interdigitated electrode material 140 and the membrane 104. In this embodiment, the field between the electrode material 140 and the membrane 104 is substantially in the X-Y plane. In some embodiments, however, the membrane 104 is not conductive or no conductive material is located below the membrane (when viewed in the X-Y plane). In these embodiments, an additional separate electrode material lead or layer (not shown) is provided that is electrically isolated from the interdigitated electrode material 140. The additional electrode material is located between each set of electrode material and a field is applied between each set of electrode material and the additional material to, for example, actuate the electrically responsive material. In this manner, the field is applied substantially in the X-Z plane.

A layer 136 of metal (e.g., approximately 500 angstroms of gold) is deposited on an inner surface 138 (i.e., the surface facing the cavity 124) of the membrane 104 to, for example, facilitate immobilization of capture agents. Biological or chemical matter binds to capture agents on the layer 136 under circumstances where the device 100 is used to quantify the matter in, for example, a fluid sample. In some embodiments, no layer 136 of metal is used.

In operation, instrument/control electronics 128 (referring to FIG. 1A) apply a time-varying electrical signal to one set of the electrode material 140 (relative to the membrane 104) to generate vibrations 112 in the suspended membrane 104. The instrument/control electronics 128 also monitor the vibrational characteristics of the membrane 104 by receiving a sensor signal from the second set of electrode material 140 relative to the membrane 104.

In one embodiment, several fluids are used in an application of the resonant device to detect the presence of biological molecules suspended in a fluid. A reference buffer fluid is exposed to the layer 136 to establish a baseline resonance response. A sample solution containing the biological molecules is flowed over the layer 136 of the device 100. At least some of the biological molecules bind to the layer 136 causing the resonance characteristics of the device 100 to change. The resonance of the device 100 with bound biological molecules is compared with the baseline resonance to determine how much biological material is bound to the layer 136 of the device 100.

In one embodiment, when liquid is in contact with the cavity side 124 of the membrane 104, the maximal response of the plate structure is around 15-25 MHz as dictated by various properties of the device 100 (e.g., length, thickness and stiffness of the membrane 104). In one embodiment, the instrument/control electronics 128 compare a reference signal to the signal from the second set of electrode material 140 to determine the changes in the relative magnitude and phase angle of the signal as a function of frequency. The instrument/control electronics 128 interpret these changes to detect the presence of, for example, a targeted analyte that has attached to the layer 136 of the membrane 104. In some embodiments, the instrument/control electronics 128 also determines, for example, the concentration of the targeted analyte on the layer 136 of the membrane 104.

In some embodiments, the substrate 108, electroactive material 132 and electrode material 140 are parts of a device 100 that are incorporated into an integrated circuit package using techniques known in the art. In some embodiments, the device 100 is a filter device (e.g., a surface acoustic wave (SAW) device or a film bulk acoustic resonator (FBAR) device). In some embodiments, the device 100 is a sensor used, for example, to detect or measure biological, chemical or physical properties of fluids or gases.

Figure 1B:
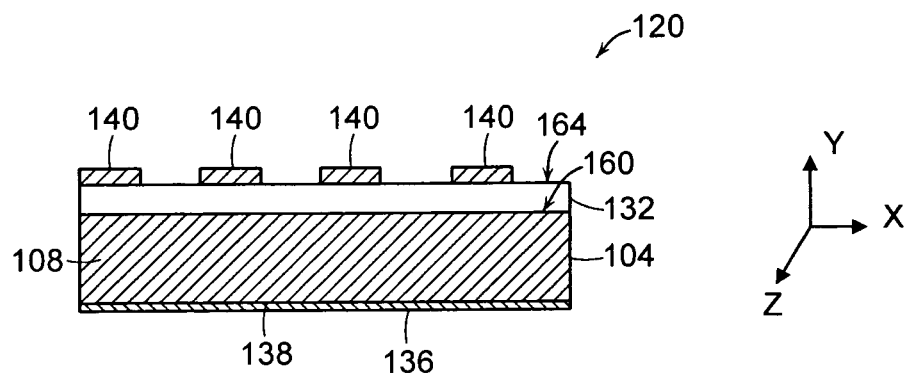
FIG. 1B is a schematic illustration of a portion of the device of FIG. 1A.

Devices, such as the device 100 of FIGS. 1A and 1B, however, have suboptimal performance properties. The devices tend to have non-isolated resonance modes, high loss, wide resonance bands, and unstable and non-repeatable operating characteristics. Additionally, the response of these devices is sensitive to the boundary conditions of the structure defined by, for example, the suspended structure of 142 that is defined by the combination of cavity 124, the membrane 104, electrically responsive material 132, and other materials located on, below, or between membrane 104 and electrically responsive material 132. In some embodiments, it is desirable during fabrication to control the dimensions of the suspended structure 142 along the X-axis and the Y-axis, the alignment of the electrode material 140 relative to the boundaries of the suspended structure 142, and the compliance of the regions in proximity to the boundaries of the suspended structure 142 to achieve repeatable performance of the device 100.

Figure 2:
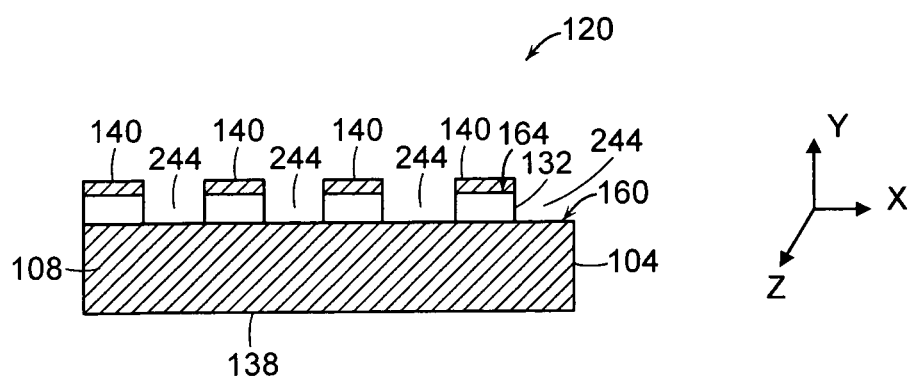
FIG. 2 is a schematic illustration of a portion of an electrically responsive device, according to an illustrative embodiment of the invention.

FIG. 2 is a schematic illustration of a region 120 of a electrically responsive device (for example, the device 100 of FIG. 1A) incorporating principles of the present invention that overcome the limitations of prior art devices. The region 120 of the device has a membrane 104 and an electrically responsive material 132 (e.g., AlN) distributed over portions of the membrane 104. In this embodiment, the region 120 of the electrically responsive device also has two sets of interdigitated electrode material 140 located over the electrically responsive material 132.

This embodiment of the region 120 of the electrically responsive device is different from the region 120 of the device of FIG. 1B in that there are locations 244 that do not have electrically responsive material. The lack of electrically responsive material in locations 244 substantially modifies at least one resonance mode of response of the device by altering a structural property of the device. In this embodiment, the lack of material in locations 244 alters the stiffness of the device along the X-Axis of the device. Referring to FIG. 2, the locations 244 lacking electrically responsive material enforce a desired modal response of the electrically responsive device such that, when combined with electrical stimulus applied by electronics (e.g., the electronics 128 of FIG. 1A) to the electrode material 140, results in improved modal isolation and dynamic amplification.

Modal isolation is the narrow band preferred response of one resonance mode over other resonance modes exhibited by the electrically responsive device in a particular frequency range. Improved dynamic amplification results from the improved alignment of the device mode shape with the transductions means (i.e., position of electrode material 140 relative to electrically responsive materials 132). Electrically responsive devices having locations 244 that lack electrically responsive material also improve dynamic amplification of signals associated with the devices due to the reduction in material damping that would otherwise occur if electrically responsive material was located in locations 244.

Device locations 244 lacking electrically responsive material 132 are achieved in a variety of ways. By way of example, locations 244 can be created by selective removal of the electrically responsive material 132. In some embodiments, the locations 244 are created by selective application or deposition of electrically responsive material 132 in only those locations where it is desirable to have the electrically responsive material 132.

In this embodiment (referring to FIG. 2) the locations 244 completely lack electrically responsive material 132. Alternative embodiments are contemplated, however, where only a portion of the electrically responsive material is lacking in locations 244. In some embodiments, the electrically responsive material remaining in locations 244 can have a, for example, square, rectangular, semicircular, or wedge shape. In some embodiments, the electrically responsive material 132 in locations 244 has an irregular shape (e.g., rough texture).

By way of example, an isotropic etching process can be used to produce a semicircular shape when viewed in the X-Y plane. In some embodiments, an etching process that removes some or all of the electrically responsive material 132 in locations 244 also removes some of the electrically responsive material 132 in adjacent locations (e.g., below locations of electrode material 140). Without departing from the scope of the invention, in some embodiments one or more materials used to fabricate an electrically responsive device that incorporates principles of the present invention can have a non-uniform dimension (e.g., thickness when viewed in the X-Y plane). By way of example, fabrication techniques exists that allow for producing a layer of electrically responsive material that has a generally smoothly varying thickness along the X-axis and/or Z-axis. In this manner, the stiffness of the device 100 can be varied along the X-axis and/or Z-axis in accordance with principles of the present invention.

In some embodiments, a controllable etch process is used to modify or modulate structural properties of one or more layers of the electrically responsive device. In some embodiments, uniformity and repeatability of the etched depth is controlled to within about 500 Angstroms. In some embodiments, about 1500 Angstroms of electrically responsive material is removed (e.g., etched) in locations 244 of the electrically responsive device. In some embodiments, the steps used to fabricate the electrically responsive device are performed in an order that protects the electrically responsive material during processing until it is desired that the electrically responsive material be, for example, etched.

In some embodiments, a filler material is subsequently applied in the locations 244. The filler material can have a stiffness that is dissimilar to the stiffness of the electrically responsive material 132. The filler material (or another material) can be applied to create a substantially flat or planar surface in the X-Z plane of the electrically responsive device.

The principles of the present invention can be achieved in other embodiments of the invention. One or more properties of the device can be altered along one or more of the X-Axis, Y-Axis or Z-Axis of the electrically responsive device. The stiffness of the electrically responsive device can be altered by removing material from, for example, the substrate material or the electrically responsive material (e.g., the substrate material 108 or the electrically responsive material 132 of FIG. 2). The stiffness of the device can be altered by modifying or doping certain portions of the substrate material or the electrically responsive material. The distribution of mass over a portion of the device can also be altered to modify at least one resonant mode of the device.

In one embodiment, the distribution of stiffness and/or mass is altered by adding material (e.g., a material compatible with MEMS processing techniques) in a specific pattern over the device (e.g., over electrode material, electrically responsive material and/or substrate material). In some embodiments, material is added because it is easier to control the deposition process rather than an etching process where, for example, timing associated with etching has more variability.

In some embodiments, the electrically responsive device includes just a membrane (e.g., the membrane 104 of FIG. 1A). The membrane is adapted such that the portion 120 of the membrane has the features illustrated in FIG. 2. In some embodiments, a cartridge for detecting an analyte incorporates the electrically responsive device and a fluid channel. The electrically responsive device is located within the fluid channel or defines at least a portion of a surface of the fluid channel. The cartridge can be a consumable component of an apparatus and can be removed and replaced. Some embodiments also can include fluid control devices (e.g., plugs, obstructions and baffles) that alter the flow through the cartridge or an apparatus that incorporates the cartridge.

One embodiment of the invention is a kit used in detection of an analyte or other target material (e.g., chemical or biological matter). The kit includes the cartridge which includes the electrically responsive device and fluid channel. The electrically responsive device also includes a first component (e.g., material, film, substance or chemical) that is capable of binding to an analyte. The component or material can be a substance bound to a surface of the electrically responsive device (e.g., a surface of layer 136 of the membrane 104 of the device 100 of FIGS. 1A and 2). In some embodiments, the kit also includes particles (e.g., beads) that include a second component capable of binding to the analyte. The particles can be, for example, separate from the cartridge or located within the cartridge in, for example, a cavity or channel located in the cartridge. In other embodiments, a sample containing the analyte is mixed with the particles in the cartridge or external to the cartridge. At least some of the analyte binds to the particles. The particles are then flowed past the surface of the electrically responsive device having the first component. The analyte bound to the particles then bind to the second component. Then, in the manner described herein previously, electronics (e.g., the electronics 128 of FIG. 1A) are used by, for example, an operator or automatically by a processor, to detect the presence and/or quantify the amount of analyte present.

In some embodiments, a gas phase selective absorptive layer is provided on one or more surfaces of the materials use to fabricate the electrically responsive device. The absorptive layer selectively binds or adheres to a gas that is exposed to the electrically responsive device. Structural properties (e.g., mass, stiffness, loss) of the absorptive layer change based on the degree of diffusion of the gas into the absorptive layer. These structural changes are determined based on changes in pass band characteristics of device. In this manner, the presence an d/or quantity of gas can be determined for a sample containing the gas that is provided to the device.

Figure 9:
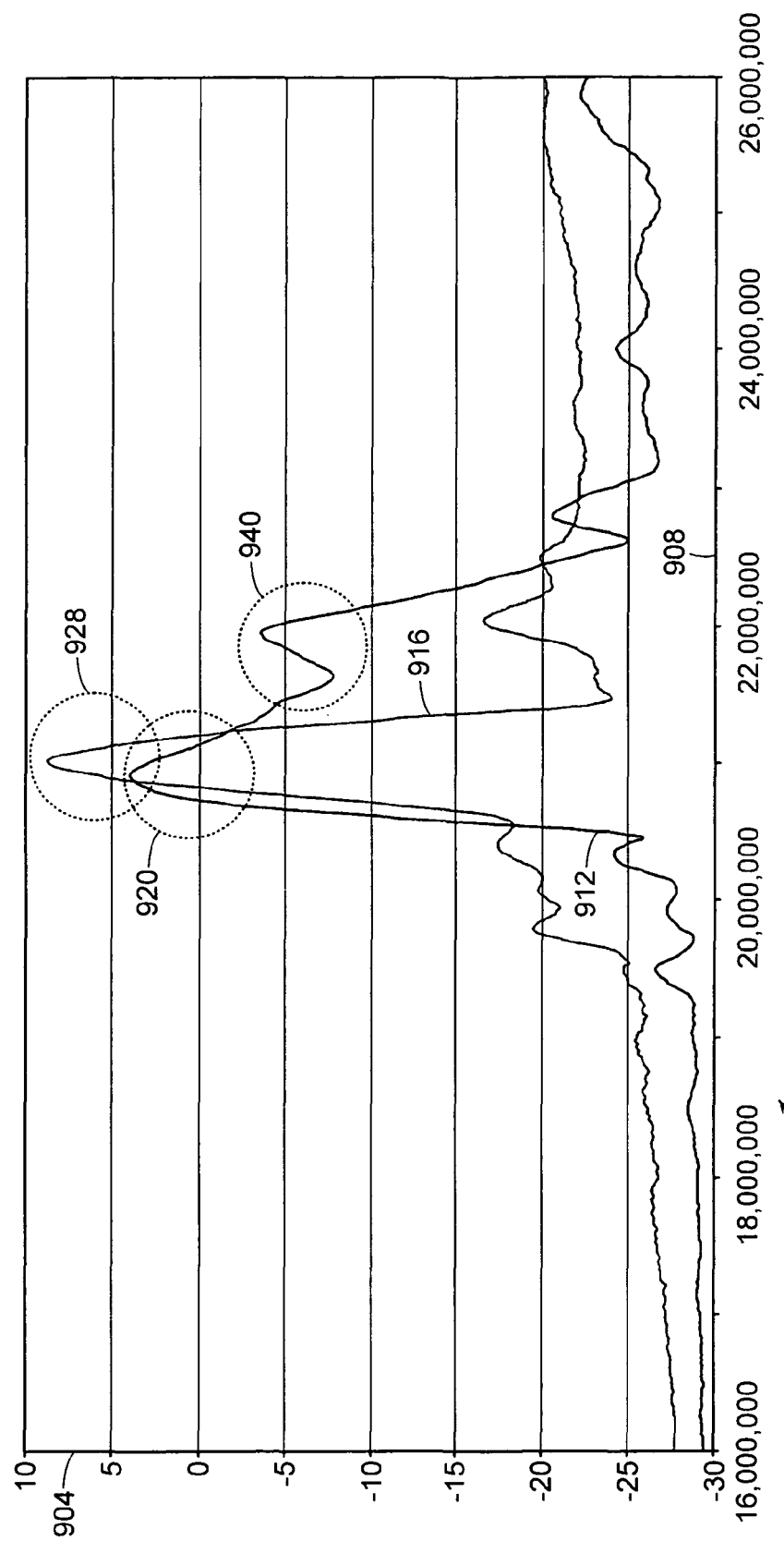
FIG. 9 is a graphical representation of transfer function magnitudes versus frequency for a resonant device incorporating principles of the present invention and a resonant device not incorporating principles of the present invention.

In some embodiments, liquid is provided to one or more surfaces of the electrically responsive device. Coupling (e.g., acoustic coupling) of the liquid to the electrically responsive device loads the device and produces a loaded device pass band (curves 912 and 916 of FIG. 9 are transfer function plots for fluid loaded electrically responsive devices). Changes in the exposed liquid properties are determined from changes in device pass band characteristics of the curves as compared with similar curves obtained in the absence of fluid loading.

Figure 3:
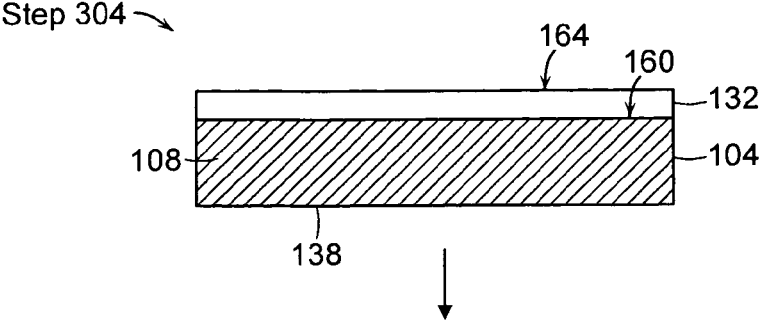
FIG. 3 is a schematic illustration of different phases of a method for fabricating an electrically responsive device, according to an illustrative embodiment of the invention.
Figure 3:
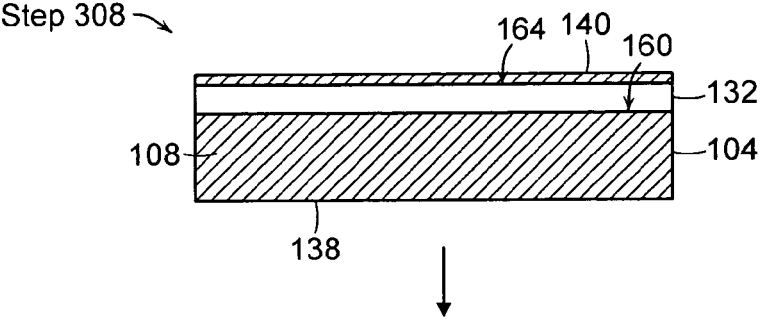
Figure 3:
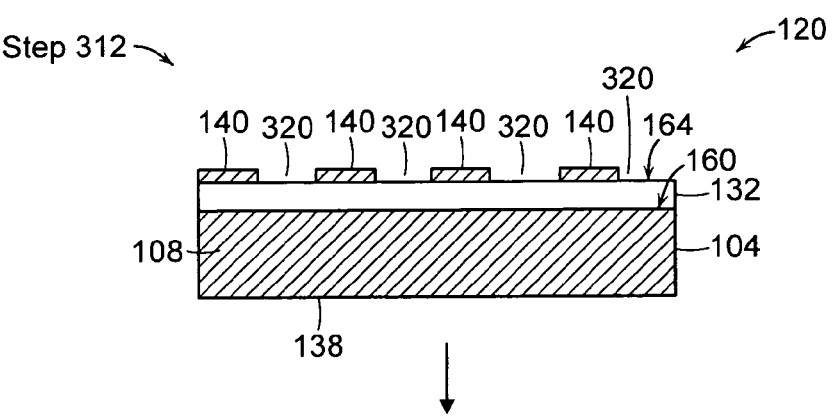
Figure 3:
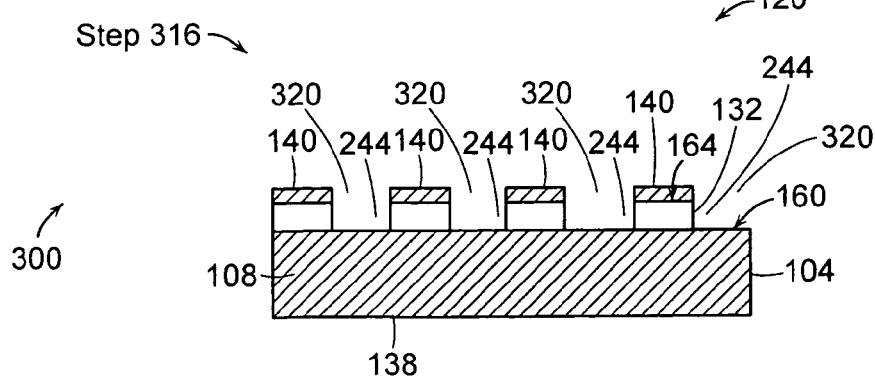

FIG. 3 is a schematic side illustration showing different phases of a method 300 for fabricating an electrically responsive device (e.g., a resonant device comprising the device region 120 of FIG. 2), according to an illustrative embodiment of the invention. The method 300 involves applying (step 304) an electrically responsive material 132 (e.g., an electroactive material) over at least a portion of a surface 160 of a membrane 104 of a substrate material 108. In one embodiment, the electrically responsive material 132 is applied to the surface 160 of the membrane 104 by reactive sputtering of the electrically responsive material 132. Other suitable methods may, alternatively, be used to apply the electrically responsive material 132 over the substrate material 108.

The method 300 also involves applying (step 308) an electrode material 140 over at least a portion of a surface 164 of the electrically responsive material 132. Various methods may be used to apply the electrode material 140. In one embodiment, the electrode material 140 is applied by physical vapor deposition (e.g., e-beam evaporation plating or sputtering).

In some embodiments, an optional step is performed prior to applying (step 308) the electrode material 140. In some embodiments, an intermediate layer is first applied to the surface 164 of the electrically responsive material 132, prior to application of the electrode material 140. In one embodiment, the intermediate layer improves the subsequent bonding of the electrode material 140 to the electrically responsive material 132. In some embodiments, additional layers of material are deposited over the electrode material 140 to coat or protect the underlying material or to alter structural properties according to principles of the present invention.

The method 300 also involves selectively removing (step 312) at least one region 320 of the electrode material 140 exposing the electrically responsive material 132. The removal step (step 312) can involve any suitable removal process (e.g., a suitable semiconductor material removal process). In this embodiment, the electrode material 140 is removed using etch processing (e.g., one or more of wet etching, dry etching, plasma etching, laser assisted etching, laser ablation, ion beam milling, and electron beam etching). Removing the regions 320 of the electrode material 140 produces a plurality of locations of the electrode material 140 on the surface 164 of the electrically responsive material 132.

The method 300 also involves selectively removing (step 316) at least some of the electrically responsive material 132 in the region 320, producing regions 244. Step 316 can be conducted using the various types of removal processes discussed herein (e.g., etch processing). In this embodiment, all the electrically responsive material is removed in the region 320 corresponding to the electrode material 140. In this manner, regions 244 of the electrically responsive material 132 are substantially the same in geometry along the X-Axis and Z-Axis as the regions 320 of the electrode material 140.

In some embodiments, however, only a portion of the electrically responsive material 132 is removed in the region 320, resulting in regions 244 of the electrically responsive material 132 being smaller in geometry than the regions 320 of the electrode material 140 along the X-Axis and Z-Axis. In some embodiments, removal of the electrode material (step 308) and removal of the electrically responsive material (step 312) are conducted with a single removal step.

Figure 4:
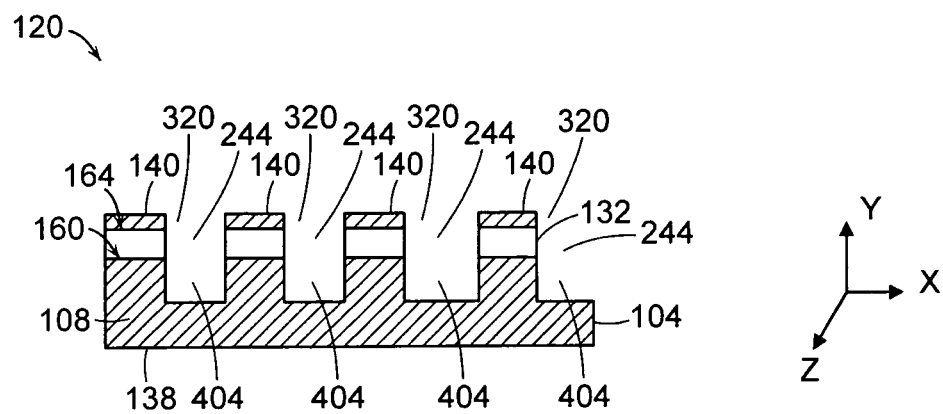
FIG. 4 is a schematic illustration of a portion of an electrically responsive device, according to an illustrative embodiment of the invention.

FIG. 4 is a schematic illustration of a region 120 of an electrically responsive device, according to an illustrative embodiment of the invention. In this embodiment, the substrate 108 is removed in regions 404 of the region 120 of the device. The regions 404 of the substrate 108 are substantially the same in geometry along the X-Axis and Z-Axis as both the regions 320 of the electrode material 140 and the regions 244 of the electrically responsive material 132. Creating regions 404 of the substrate 108 enforces a desired modal response of the device. In other embodiments, regions 320, 244 and 404 have different geometries from each other along the X-Axis and Z-Axis.

Figure 5:
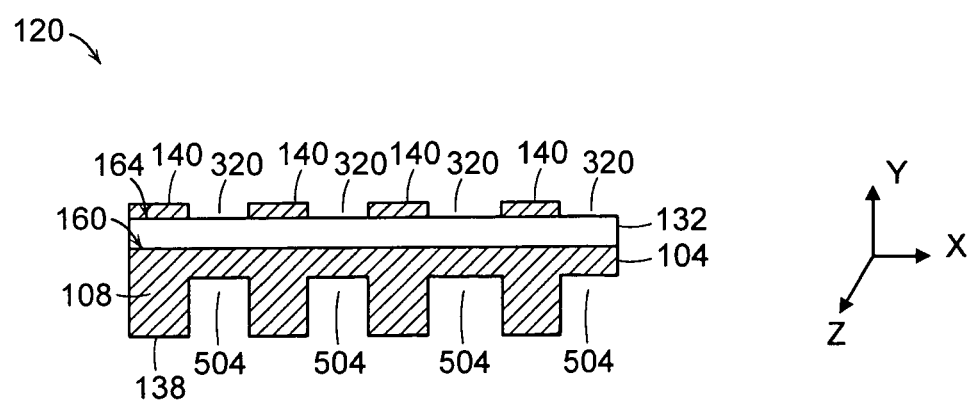
FIG. 5 is a schematic illustration of a portion of an electrically responsive device, according to an illustrative embodiment of the invention.

FIG. 5 is a schematic illustration of a region 120 of a membrane 104 of an electrically responsive device, according to an illustrative embodiment of the invention. The region 120 of the membrane 104 has a layer of electrically responsive material 132 disposed over a substrate 108. Electrode material 140 is located over the electrically responsive material 132. In this embodiment, a modal response of the device comprising the region 120 of FIG. 5 is modified by the removal of substrate material 108 in regions 504. The regions 504 correspond to substantially the same geometry (along the X-Axis and Z-Axis) of the electrode material 140 in the regions 320 associated with the electrode material 140.

In some embodiments, the modal response of the electrically responsive device is instead modified by creating regions (lacking substrate material) in the substrate 108 in regions located beneath the electrode material 140 along the Y-Axis. In some embodiments, at least one region 504 comprises no substrate material 108 below the electrically responsive material 132. In this manner, the electrically responsive material is not supported in this region by the substrate material 108. In this manner, the unsupported electrically responsive material can produce a cantilever electrically responsive element. In some embodiment, the cantilever electrically element is an cantilever electroactive element in which element may be actuated to bend or actuate the element.

In some embodiments, a filler material is subsequently applied in the regions 504. The filler material can have a stiffness that is dissimilar to the stiffness of the substrate material 108. In this manner, a property of the electrically responsive device also can be altered to substantially modify a resonance of the device.

FIG. 6 is a schematic illustration of a pattern 600 of electrode material, such as the electrode material 140 of FIG. 2, according to an illustrative embodiment of the invention. The pattern 600 has a sensing or receiving side 604 and an actuating or launching side 608. The sensing or receiving side 604 provides output signals from the device (e.g., the device 100 of FIGS. 1A and 1B). The actuating or launching side 608 is used to provide input signals to the device. The side 604 has two sets of electrode material locations 140a and 140b (generally 140) similarly as described previously herein regarding, for example, the electrode material 140 of FIG. 2. Likewise, the side 608 has two sets of electrode material locations 140c and 140d (generally 140) similarly as described previously herein.

In operation in one embodiment, time varying, opposing polarity electrical signals are applied to the electrode material locations 140c and 140d of the side 608 to generate vibration in the membrane 104 of a resonant device. An outer edge 612 of the membrane 104 is also shown in FIG. 6. In operation, the electrode material locations 140c and 140d in combination with the electrode material locations 140a and 140b are used to measure the effects of, for example, a fluid in contact with the resonant device (e.g., a surface of the membrane 104 or a surface of a material located above or below the membrane 104). In some embodiments, the electrode material locations 140c and 140d in combination with the electrode material locations 140a and 140b are used to measure the effects of, for example, biological matter in contact with the surface of the membrane 104.

FIG. 7 is a schematic illustration of a pattern 700 of electrode material, such as the electrode material 140 of FIG. 2, according to an illustrative embodiment of the invention. The pattern 700 has a sensing or receiving side 704 and an actuating or launching side 708. The side 704 has two sets of electrode material locations 140a and 140b. Likewise, the side 708 has two sets of electrode material locations 140c and 140d. Devices according to the invention can be fabricated such that the combination of electrode material and electrically responsive material produce one or more sensing or receiving elements. Similarly, devices according to the invention, can be fabricated such that the combination of electrode material and electrically responsive material produce one or more actuating or launching elements.

In operation in one embodiment, time varying, opposing polarity electrical signals are applied to the electrode material locations 140c and 140d to generate vibrations in the membrane 104 of a resonant device. An outer edge 712 of the membrane 104 is also shown in FIG. 7. By way of example, in operation, the electrode material locations 140c and 140d in combination with the electrode material locations 140a and 140b are used to, for example, measure the effects of a fluid in contact with the resonant device.

In this embodiment, the membrane 104 has a rectangular shape as viewed in the X-Z plane. Alternative geometries for the membrane (and also, for example, the suspended structure 142 of FIG. 1) are contemplated that incorporate principles of the present invention. Further, in this embodiment, the side 704 and side 708, together, have a generally rectangular shape as viewed in the X-Z plane. Alternative geometries for one or both of sides 704 and 708 are contemplated that incorporate principles of the present invention. By way of example, the membrane 104, suspended structure 142, and the electrodes 140 (e.g., side 704 and side 708) can have a variety of shapes when viewed in the X-Z plane.

In one embodiment, the membrane 104, suspended structure 142, and sides 704 and 708 together, have a generally square shape when viewed in the X-Z plane. In another embodiment, the membrane 104 and suspended structure 142 have a generally circular shape when viewed in the X-Z plane. In this embodiment, the electrode material locations 140a, 140b, 140c and 140d, together have a generally circular shape when viewed in the X-Z plane. In this embodiment, the electrode material locations 140a, 140b, 140c and 140d are individually annular in shape (when viewed in the X-Z plane) forming generally concentric rings relative to each other.

Figure 8:
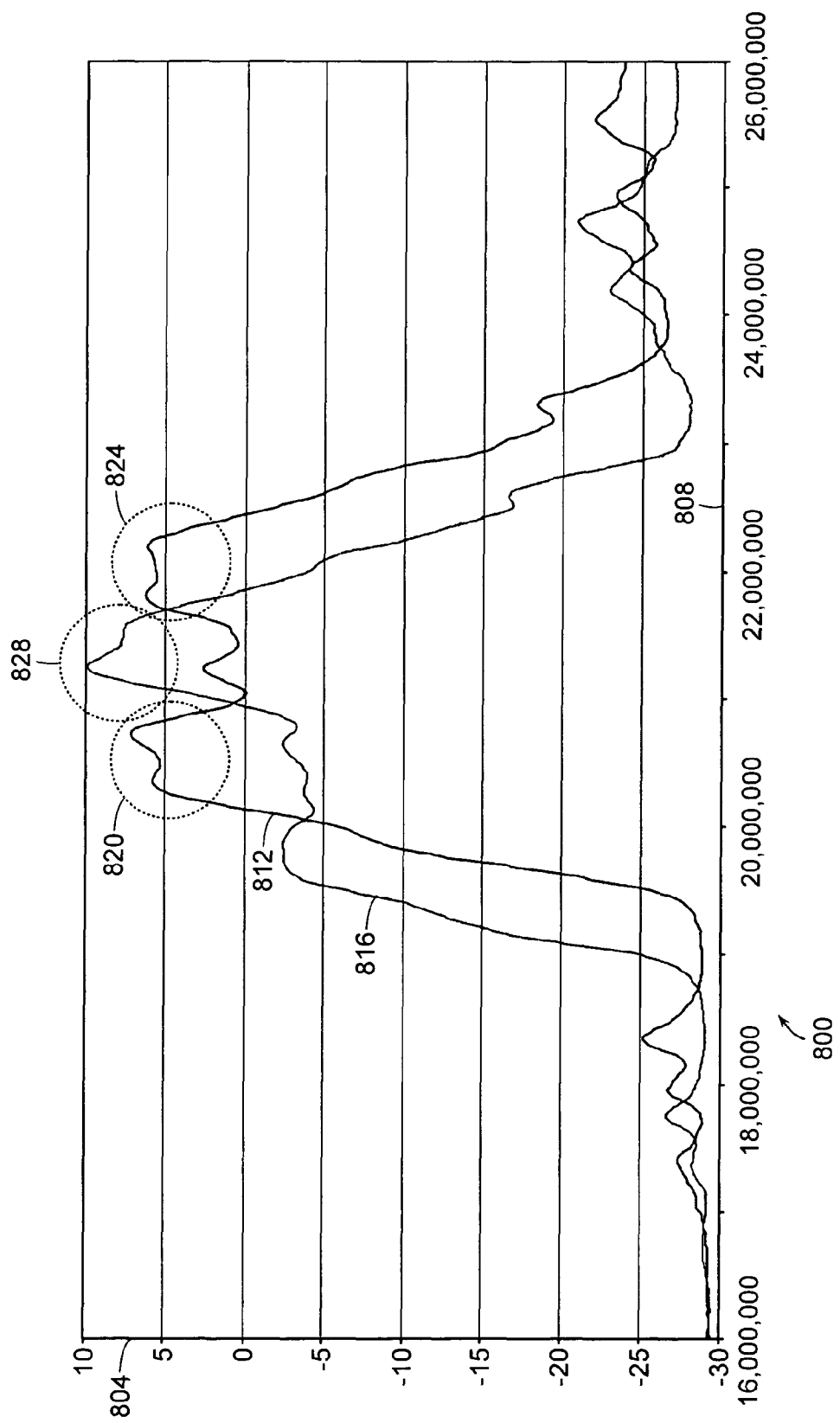
FIG. 8 is a graphical representation of transfer function magnitudes versus frequency for a resonant device incorporating principles of the present invention and a resonant device not incorporating principles of the present invention.

By way of illustration, an experiment was conducted in which data was acquired for a resonant device incorporating principles of the present invention. The experiment was conducted with a cavity and sensing surfaces of the device (e.g., the cavity 124 and surfaces within the cavity 124 of the device 100 of FIG. 1A) exposed to 1× phosphate buffered saline fluid sold by, for example, Sigma-Aldrich with offices in St. Louis, Mo. FIG. 8 illustrates a plot 800 of the transfer function magnitude obtained using the device 100 of FIG. 1A. The Y-Axis 804 of the plot 800 is the magnitude of an input signal applied to the device 100 relative to an output signal of the device 100. The X-Axis 808 of the plot 800 is frequency in Hertz (Hz).

Curve 812 is the transfer function magnitude versus frequency for an electroactive material device 100 having a region 120 that does not incorporate principles of the present invention (i.e., the region 120 of FIG. 1B). Curve 816 is the transfer function magnitude versus frequency for an electroactive material device 100 having a region 120 that incorporates principles of the present invention (i.e., the region 120 of FIG. 2). By way of reference, the resonant device 100 used in obtaining the data associated with curves 812 and 816 each had a pattern of electrode material corresponding to the pattern 600 of FIG. 6.

The curve 812 has two regions 820 and 824 corresponding to various dominant resonance modes of the electrically responsive device. Curve 816, however, has one region 828 in which resonance modes of the resonant device are relatively dominant compared to other locations on the curve 816. In this experiment, region 828 of curve 816 is a preferred pass band because it is generally isolated from adjacent resonant modes of the electrically responsive device as demonstrated by the observation that the curve 816 drops off to the left and right of region 828. In this manner, the selective removal of at least some of the material 132 that creates regions 244 of the region 120 of the device 100 of FIG. 2 substantially modifies at least one resonance mode of the device 100. Modal overlap and spillover associated with some resonance modes between about 16 MHz and about 26 MHz is reduced thereby enforcing at least one resonance mode of response of the device 100 as illustrated in the region 828 of the curve 816.

By way of illustration, another experiment was conducted in which data was acquired for a resonant device incorporating principles of the present invention. The experiment was conducted with a cavity and sensing surfaces of the device (e.g., the cavity 124 and surfaces within the cavity 124 of the device 100 of FIG. 1A) exposed to 1× phosphate buffered saline fluid sold by, for example, Sigma-Aldrich with offices in St. Louis, Mo. FIG. 9 illustrates a plot 900 of the transfer function magnitude obtained using the device 100 of FIG. 1A. The Y-Axis 904 of the plot 900 is the magnitude of an input signal applied to the device 100 relative to an output signal of the device 100. The X-Axis 908 of the plot 900 is frequency in Hertz (Hz).

Curve 912 is the transfer function magnitude versus frequency for an electroactive material device 100 having a region 120 that does not incorporate principles of the present invention (i.e., the region 120 of FIG. 1B). Curve 916 is the transfer function magnitude versus frequency for a device 100 having a region 120 that incorporates principles of the present invention (i.e., the region 120 of FIG. 2). By way of reference, the device 100 used in obtaining the data associated with curves 912 and 916 each had a pattern of electrode material corresponding to the pattern 700 of FIG. 7.

The curve 912 has a region 920 corresponding to various dominant resonance modes of the resonant device. Curve 916 has a region 928 in which at least one resonance mode of the resonant device has been modified to enforce at least one resonance mode illustrated in region 928 as compared to other locations on the curve 916. In this experiment, region 928 of curve 916 is a preferred pass band because it is generally isolated from adjacent resonant modes of the electrically responsive device as demonstrated by the observation that the curve 916 drops off to the left and right of region 928 and there is no substantial resonant mode shown to the left and right of region 928. In contrast, for example, region 920 of curve 912 does have at least one substantial resonant mode 940 that is adjacent to the region 920. In this manner, the device corresponding to curve 912 has a less preferred pass band region 920 because of the presence of the at least one resonance mode 940. The device has a preferred pass band, narrower bandwidth with respect to frequency and lower transmission loss, evidenced by a more pronounced peak in region 928 relative to the peaks in regions 920 and 940), than would otherwise be achieved without incorporating principles of the present invention. Preferred pass bands, narrower bandwidth and lower transmission loss are also achieved in the device in the absence of fluid loading.

Further, the region 928 of the curve 916 illustrates that at least one resonant mode in the region 928 has been substantially modified when compared with the comparable region 920 of curve 912. The substantial modification is due to the removal of at least some of the electroactive material 132 that creates regions 244 of the region 120 of the device 100 of FIG. 2. Modal overlap and spillover associated with some resonance modes between about 16 MHz and about 26 MHz is reduced in the region 928 of the curve 916, thereby enforcing at least one resonance mode of response of the device 100 in the region 928 of the curve 916.

Variations, modifications, and other implementations of what is described herein will occur to those of ordinary skill in the art without departing from the spirit and the scope of the invention and are considered to be encompassed thereby. Accordingly, the invention is not to be defined only by the preceding illustrative description.

What is claimed is:

1. An electrically responsive device comprising:
    a composite structure having spatially modulated structural properties comprising:
        a substrate material having a surface and defining a plane,
        an electrically responsive material over at least a portion of the surface of the substrate material, and
        an electrode material over portions of the electrically responsive material, wherein the spatially modulated structural properties comprise regions of the composite structure along which the electrode material is disposed having increased material stiffness, exclusive of the electrode material, relative to regions of the composite structure that do not include the electrode material; and
    a control device configured to excite motion of the composite structure and to sense motion of the composite structure, the motion being substantially correlated with the spatially modulated properties.

2. The device of claim 1 wherein the electrically responsive material comprises an electroactive material.

3. The device of claim 1 wherein the spatially modulated structural properties are periodic along a surface of the structure.

4. The device of claim 1 wherein the composite structure comprises a component capable of binding to biological or chemical matter.

5. The device of claim 2 wherein about 1500 Angstroms of material is removed from regions of the electroactive material to spatially modulate the structural properties of the electrically responsive material and the composite structure.

6. The device of claim 1 wherein the electrically responsive material varies in thickness along the plane of the substrate material and the electrode material has an interdigitated pattern.

7. The device of claim 1 wherein the spatially modulated structural properties are spatially modulated by adding structural material over the electrode material, the structural material having different structural properties than the electrode material.

8. The device of claim 1 or 6 wherein the spatially modulated structural properties are periodic with spatial periodicity that substantially matches one of the device's mode shapes.

9. The device of claim 1, comprising an electrode material between the substrate material and the electrically responsive material.

10. The device of claim 1, comprising a filler material applied in a cavity region of the electrically responsive material associated with the spatially modulated properties, wherein stiffness of the filler material is dissimilar to stiffness of the electrically responsive material.

11. The device of claim 1 wherein the electrically responsive material and electrode material are patterned to produce at least one launch element and at least one receiver element.

12. The device of claim 1 wherein the spatially modulated structural properties comprises the electrically responsive material having one or more thicker regions and one or more thinner regions, the thicker regions having a thickness that is greater than the thinner regions, and wherein the regions having increased material stiffness comprise the one or more thicker regions of the electrically responsive material.

13. An apparatus for detection of an analyte, the apparatus comprising:
a fluid channel;
an electrically responsive device defining at least a portion of at least one surface of the fluid channel, the electrically responsive device comprising:
a composite structure having spatially modulated structural properties comprising:
a substrate material having a surface and defining a plane,
an electrically responsive material over at least a portion of the surface of the substrate material, and
an electrode material over portions of the electrically responsive material, wherein the spatially modulated structural properties comprise regions of the composite structure along which the electrode material is disposed having increased material stiffness, exclusive of the electrode material, relative to regions of the composite structure that do not include the electrode material, and
a control device configured to excite motion of the composite structure and to sense motion of the composite structure, the motion being substantially correlated with the spatially modulated properties; and
a monitoring device to monitor at least one signal output by the electrically responsive device.

14. A cartridge for detection of an analyte, the cartridge comprising:
a fluid channel; and
an electrically responsive device, wherein the fluid channel delivers fluid to the electrically responsive device, the electrically responsive device comprising:
a composite structure having spatially modulated structural properties comprising:
a substrate material having a surface and defining a plane,
an electrically responsive material over at least a portion of the surface of the substrate material, and
an electrode material over portions of the electrically responsive material, wherein the spatially modulated structural properties comprise regions of the composite structure along which the electrode material is disposed having increased material stiffness, exclusive of the electrode material, relative to regions of the composite structure that do not include the electrode material, and
a control device configured to excite motion of the composite structure and to sense motion of the composite structure, the motion being substantially correlated with the spatially modulated properties.

15. A kit used in detection of an analyte, the kit comprising:
a cartridge comprising,
a fluid channel, and
an electrically responsive device defining at least a portion of at least one surface of the fluid channel and comprising a first component which specifically binds the analyte to a surface of the device, the device comprising:
a composite structure having spatially modulated structural properties comprising:
a substrate material having a surface and defining a plane,
an electrically responsive material over at least a portion of the surface of the substrate material, and
an electrode material over portions of the electrically responsive material, wherein the spatially modulated structural properties comprise regions of the composite structure along which the electrode material is disposed having increased material stiffness, exclusive of the electrode material, relative to regions of the composite structure that do not include the electrode material, and
a control device configured to excite motion of the composite structure and to sense motion of the composite structure, the motion being substantially correlated with the spatially modulated properties; and
particles comprising a second component which specifically binds the analyte.

16. An electrically responsive device comprising:
a composite structure having spatially modulated structural properties that are periodic along a surface of the composite structure, the composite structure comprising:
a substrate material having a surface and defining a plane,
an electrically responsive material over at least a portion of the surface of the substrate material, and
an electrode material over portions of the electrically responsive material, wherein the spatially modulated structural properties comprise regions of the composite structure along which the electrode material is disposed having increased material stiffness, exclusive of the electrode material, relative to regions of the composite structure that do not include the electrode material; and
a control device configured to excite motion of the composite structure and to sense motion of the composite structure, the motion being substantially correlated with the spatially modulated properties.

17. The device of claim 16 wherein the spatially modulated structural properties are periodic with spatial periodicity that substantially matches on of the device's mode shapes.

18. An electrically responsive device comprising:
   a composite structure comprising:
      a substrate material having a surface and defining a plane;
      an electrically responsive material over at least a portion of the surface of the substrate material;
      an electrode material over portions of the electrically responsive material; and
      a structural material over at least a portion of the electrode material, the structural material having different structural properties than the electrode material and providing the composite structure with spatially modulated structural properties by forming regions of the composite structure along which the electrode material is disposed having increased material stiffness, exclusive of the electrode material, relative to regions of the composite structure that do not include the electrode material, and
   a control device configured to excite motion of the composite structure and to sense motion of the composite structure, the motion being substantially correlated with the spatially modulated properties.

* * * * *